(12) United States Patent
Cude

(10) Patent No.: US 7,955,309 B2
(45) Date of Patent: *Jun. 7, 2011

(54) SYRINGE PLUNGER JACKET WITH EXPANDABLE SEAL

(75) Inventor: J. Michael Cude, Woodburn, KY (US)

(73) Assignee: Coeur, Inc., Lebanon, TN (US)

( * ) Notice: Subject to any disclaimer, the term of this patent is extended or adjusted under 35 U.S.C. 154(b) by 364 days.

This patent is subject to a terminal disclaimer.

(21) Appl. No.: 11/279,644

(22) Filed: Apr. 13, 2006

(65) Prior Publication Data
US 2007/0088270 A1 Apr. 19, 2007

Related U.S. Application Data

(60) Provisional application No. 60/594,496, filed on Apr. 13, 2005.

(51) Int. Cl.
*A61M 5/315* (2006.01)

(52) U.S. Cl. .......... 604/218; 604/219; 604/222

(58) Field of Classification Search .......... 604/212–217, 604/181, 187, 151–155, 218, 219, 230, 222; 600/431–435; 3/212–217

See application file for complete search history.

(56) References Cited

U.S. PATENT DOCUMENTS

| | | | |
|---|---|---|---|
| 3,147,753 A | 9/1964 | Nogier et al. | |
| 3,623,474 A | 11/1971 | Heilman et al. | |
| 3,631,847 A | 1/1972 | Hobbs, II | |
| 3,890,956 A * | 6/1975 | Moorehead | 600/578 |
| 4,041,934 A | 8/1977 | Genese | |
| 4,201,209 A | 5/1980 | LeVeen et al. | |
| 4,214,507 A | 7/1980 | Hock et al. | |
| 4,266,559 A | 5/1981 | Akhavi | |
| 4,340,067 A | 7/1982 | Rattenborg | |
| 4,411,275 A * | 10/1983 | Raitto | 600/576 |
| 4,704,105 A | 11/1987 | Adorjan et al. | |
| 4,874,372 A | 10/1989 | McArthur et al. | |
| 5,314,416 A | 5/1994 | Lewis et al. | |
| 5,383,864 A * | 1/1995 | van den Heuvel | 604/218 |
| 5,397,313 A | 3/1995 | Gross | |

(Continued)

FOREIGN PATENT DOCUMENTS

JP 02-220670 3/1990

(Continued)

OTHER PUBLICATIONS

Office Action from U.S. Appl. No. 11/760,040—Apr. 20, 2009—22 pages.

*Primary Examiner* — Kevin C Sirmons
*Assistant Examiner* — Larry R Wilson
(74) *Attorney, Agent, or Firm* — Hahn Loeser & Parks LLP

(57) ABSTRACT

A syringe plunger/jacket assembly may comprise a flexible jacket attached to a rigid plunger. The jacket may comprise at least two sealing rings (front and rear) that prevent fluid from leaking out of the rear of the barrel during injection of fluid from the syringe. The rear sealing ring may not contact or seal the interior surface of the syringe barrel in an unloaded state. In the loaded state, when force is applied in the direction of the forward discharge end of the syringe, pressure is created on the jacket. This condition causes the rear seal to expand and contact and/or seal the interior surface of the syringe barrel.

9 Claims, 2 Drawing Sheets

U.S. PATENT DOCUMENTS

| | | | |
|---|---|---|---|
| 5,735,825 A * | 4/1998 | Stevens et al. | 604/218 |
| 5,788,677 A | 8/1998 | Botich et al. | |
| 5,868,710 A | 2/1999 | Battiato et al. | |
| 5,902,276 A | 5/1999 | Namey, Jr. | |
| 5,925,022 A | 7/1999 | Battiato et al. | |
| 6,004,292 A | 12/1999 | Battiato et al. | |
| 6,017,330 A | 1/2000 | Hitchins et al. | |
| 6,159,183 A | 12/2000 | Neer et al. | |
| 6,183,441 B1 | 2/2001 | Kriesel et al. | |
| 6,224,577 B1 | 5/2001 | Dedola et al. | |
| 6,254,572 B1 | 7/2001 | Knipfer et al. | |
| 2004/0116854 A1 | 6/2004 | Abulhaj et al. | |
| 2004/0215149 A1 | 10/2004 | Hjertman | |
| 2004/0254543 A1 | 12/2004 | Griffiths | |
| 2005/0033237 A1 | 2/2005 | Fentress et al. | |
| 2005/0224730 A1 | 10/2005 | Fago et al. | |
| 2007/0179449 A1 | 8/2007 | Berman et al. | |

FOREIGN PATENT DOCUMENTS

| | | |
|---|---|---|
| JP | 11-226125 | 8/1999 |

* cited by examiner

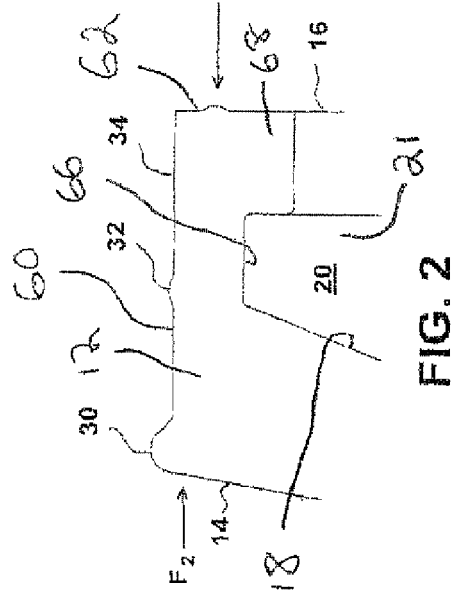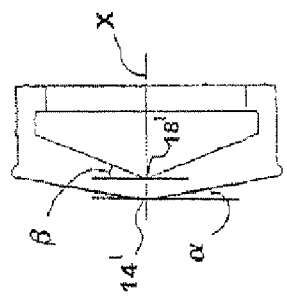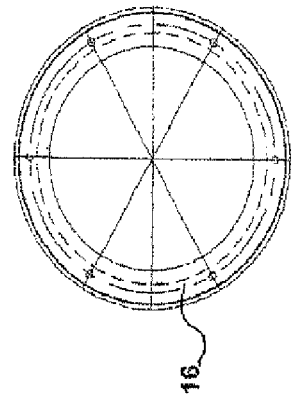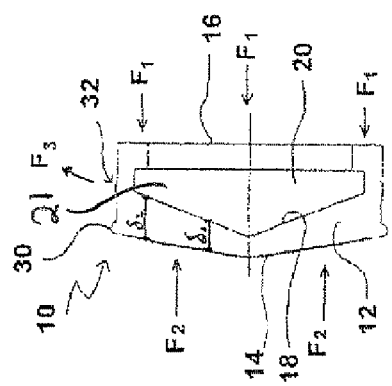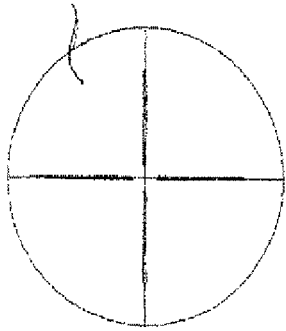

SYRINGE PLUNGER JACKET WITH EXPANDABLE SEAL

TECHNICAL FIELD

The present invention relates to syringes used in conjunction with power injectors. More particularly, the present invention relates to syringe plunger jackets having an expandable safety seal.

BACKGROUND OF THE INVENTION

Power injectors for injecting fluid into animals are well known in the art. A typical power injector comprises an injector head, having a syringe mount, and a drive ram reciprocally mounted thereon. This syringe is mounted to the injector in either a breach-load manner or a front load manner. The syringe can either be pre-filled or empty, i.e., the user must first draw contrast into the syringe before injecting fluid.

Syringes for power injectors are also well known in the art. As stated in the preceding paragraph, the syringe can be a front load type, in which the rear end of the syringe is inserted into the injector to attach the syringe to the injector. Additionally, the syringe could be breach loaded, such that, for example, a face plate of the injector is rotatable and the syringe is loaded through the rear the face plate, front end first.

A drive ram of the injector may attach to the plunger of the syringe to move the plunger forward relative to the syringe, to expel fluid from the discharge end of the syringe. In typical injection procedures, the pressure generated by the forward translation of the plunger can range from about 100 psi to 1200 psi. To ensure that contrast fluid from the syringe does not leak past the plunger, plunger assemblies typically comprise at least two (2) integral sealing rings that contact the inside surface of a syringe barrel. Typically, the forwardmost sealing ring performs the majority of the sealing process, and the rearward most sealing ring is a backup safety seal in case the forwardmost ring fails.

One problem with the plungers having two (2) seal sealing rings is that, once installed in the syringe, sterilization of the area between the two (2) sealing rings is difficult. With most materials, it is difficult for the sterilization gas to reach the area between the two (2) sealing rings. Accordingly, there is a need for a syringe jacket (seal) that overcomes the deficiencies in the prior art. This design eliminates the difficult-to-sterilize space between the two seals when the plunger is installed in the syringe. Accordingly, the present invention is hereby presented.

SUMMARY OF THE INVENTION

A syringe plunger/jacket assembly may comprise a flexible jacket attached to a rigid plunger. The jacket may comprise at least two sealing rings (front and rear) that prevent fluid from leaking out of the rear of the barrel during injection of fluid from the syringe. The rear sealing ring may not contact or seal the interior surface of the syringe barrel in an unloaded state. In the loaded state, when force is applied in the direction of the forward discharge end of the syringe, the plunger jacket assembly is moving forward relative to the syringe barrel, creating pressure on the jacket. This condition causes the rear seal to expand and contact and/or seal the interior surface of the syringe barrel.

As such, one aspect of the invention may comprise a plunger assembly for a syringe, the plunger assembly comprising: a plunger body; and a jacket at least partially covering the plunger body, the jacket having a front sealing ring and a rear sealing ring, wherein the front sealing ring has a larger outer diameter than the rear sealing ring.

A second aspect of the invention may comprise a syringe assembly, comprising: a barrel having a generally cylindrical main body portion having an interior surface and an exterior surface, a closed forward end having a discharge aperture, and an open rear end; a plunger assembly located at least partially within the barrel, the plunger assembly including a plunger body and a jacket at least partially covering the plunger body; wherein, the plunger jacket comprises a forwardmost sealing ring on a radially-outward surface and at least one auxiliary sealing ring on a radially-outward surface spaced rearwardly of the forwardmost sealing ring, and wherein the at least one auxiliary sealing ring forms a seal between the plunger assembly and the barrel only when a force is applied to the plunger assembly in the direction of the discharge aperture.

A third aspect of the invention may comprise a syringe plunger jacket having an axis, and comprising: a forward surface; an intermediate surface; and, a rear surface, wherein the jacket includes a recess extending forwardly from the rear surface and terminating at the intermediate surface, and wherein, a thickness as measured between the forward surface and intermediate surface increases as the distance from the axis increases.

BRIEF SUMMARY OF THE DRAWINGS

FIG. 1 is a cross-sectional view of a preferred embodiment of a plunger jacket assembly, in accordance with an embodiment of the present invention.

FIG. 2 is a detailed view of a portion of the plunger jacket assembly of FIG. 1.

FIG. 3 is a front view of the jacket of FIG. 1.

FIG. 4 is a rear view of the jacket of FIG. 1.

FIG. 5 is another cross-sectional view of the jacket of FIG. 1, illustrated with angles α and β.

DETAILED DESCRIPTION OF EMBODIMENTS OF THE INVENTION

Figure 6:
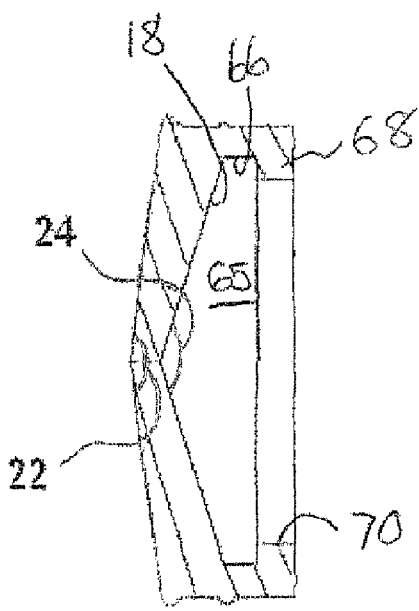
FIG. 6 is another cross-sectional view of the jacket of FIG. 1, illustrated with opening angles of the front surface and intermediate surface.
Figure 7:
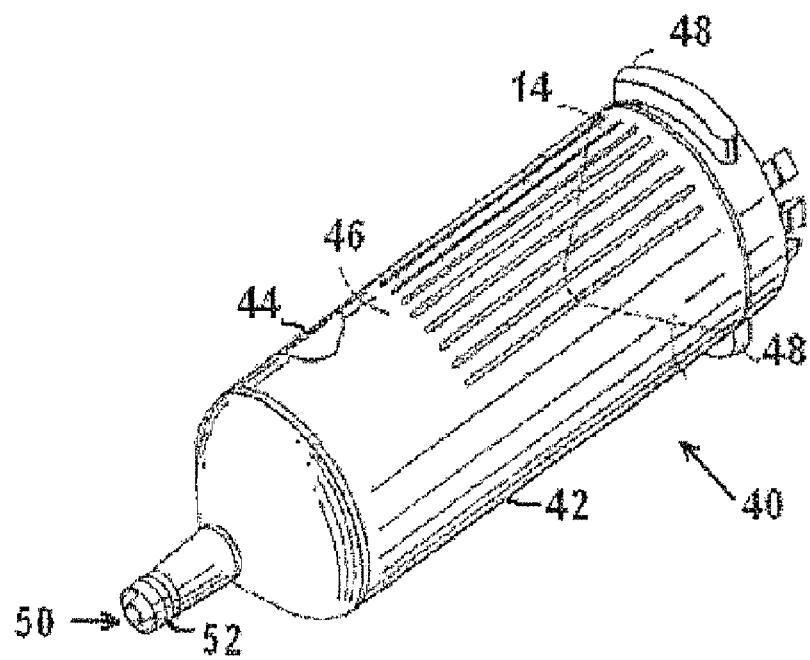
FIG. 7 is a perspective view of a syringe assembly.

The present invention will now be described in greater detail with reference to the appended drawings.

An embodiment of a syringe plunger-jacket assembly ("assembly") with expandable seal, generally identified by reference 10, is illustrated in FIGS. 1-6. The assembly 10 generally comprises a flexible jacket 12 and rigid plunger 20 (partially shown). The plunger 20 of the assembly 10 attaches to a drive ram of an injector, which moves the assembly forward to dispel contrast fluid from the syringe.

Jacket 12 may generally comprise a conical or frustoconical front surface 14, although the specific shape of front surface 14 may be dependent on the shape of the forward discharge end of the syringe barrel, i.e., the front surface 14 may be the same angularity as the forward discharge end of the syringe. Syringe jacket 12 may be connected to any of a plurality of types and shapes of plungers 20, as are known in the art. For example, the plunger may have a plurality of opposed hook members that attach the plunger to the drive ram of the power injector. Alternatively, the plunger 20 may have a rearwardly extending projection that is attachable to the drive ram. Any other drive ram-plunger connections could be utilized without deviating from the scope of the present invention, as well. Alternatively, the plunger may comprise an elongated portion extending rearwardly from the syringe barrel, as in known in hand-actuated syringes and syringes for syringe pumps.

As shown in FIGS. 1 and 2, plunger 20 has a plunger body 21 and a plunger neck 16 extending rearward therefrom. Plunger neck 16 has a smaller diameter than plunger body 21. Jacket 12 has a generally cylindrical outer wall 60 that extends rearward of the front surface 14. Outer wall 60 terminates at an end 62. The jacket 12 conforms to plunger 20 and defines a cavity 65 (FIG. 6) that receives plunger body 21. Cavity 65 is defined by an intermediate surface 18 and a cylindrical inner wall 66 that extends rearward from intermediate surface 18. As shown, inner wall 66 has a constant diameter. A neck portion 68 of jacket 12 may extend radially inward from outer wall 60 and inward of inner wall 66 to form a lip 69 that wraps jacket 12 around plunger body 21. The lip 69 defines an opening 70 that has a smaller diameter than cavity 65 and is adapted to receive neck 16 of plunger 20 (FIG. 1).

An exemplary configuration for the assembly 10 that enables seal 32 to expand during expulsion of fluid from the syringe is explained hereinafter. As illustrated in FIG. 1, the syringe jacket 12 may comprise front surface 14 and intermediate surface 18 that may contact the front of the plunger 20. Both the front surface 14 and intermediate surface 18 may comprise an apex 14' and 18'. Angle $\alpha$ is the angle formed between the front surface 14 and a line tangential to the apex 14' of the front of the jacket and perpendicular to bisecting line X. In comparison, $\beta$ is the angle formed between the intermediate surface 18 and a line tangential to the apex 18' and perpendicular to bisecting line X.

Angle $\beta$ is, in this embodiment, larger than Angle $\alpha$. In other words, as shown in FIG. 6, the opening angle 22, if the front and intermediate surfaces are conical-shaped, of the front cone 14 may be greater than the opening angle 24 of the intermediate cone 18. This differing angle results in a jacket 12 that, as measured from front surface 14 to intermediate surface 18 in a direction parallel to bisecting line X, thicker the farther radially outward that is measured. This different thickness is exemplified in FIG. 1, wherein length $\delta_1$ is less than $\delta_2$.

During an injection of fluid from the syringe, a force $F_1$ is applied by, for example, the drive ram of the injector to the rear end of the syringe plunger assembly 10 and in the direction of the forward discharge end of the syringe. Since the syringe barrel is filled with contrast solution, the contrast solution creates an opposing force $F_2$ in a direction opposite of $F_1$. The assembly 10 therefore undergoes a compression as a result of rearward force $F_1$ and forward force $F_2$. As a result, Force $F_3$ is generated, which causes the diameter of jacket 12 to increase. At the same time, seal 32 expands radially and contacts and/or seals against the interior surface of a syringe barrel.

It is contemplated that the jacket 12 can be manufactured from any suitable flexible material. For example, chlorobutyl is a typical material used in syringe jackets 20; however, any suitable flexible material that has a moderate to low durometer may be appropriate. Materials with low durometers, are potentially better suited for this application because softer materials tend to be change shape or deform more readily under pressure. However, alternatively, the material must be rigid enough to withstand major deformation.

It is contemplated that the gap between the interior of the syringe barrel and the expandable seal 32 may be on the order of 0.0010 inch, such that very little expansion is needed to form a useful seal. However, it is contemplated that any resting gap between the syringe barrel and the expandable seal 32 is contemplated, as long as the expandable seal contacts the interior of the syringe barrel during customary injection of fluid from the syringe. Without limiting the scope of the invention, the particular application may have a gap ranging from 0.005" to 0.020." It is also contemplated that the expandable seal 32 may actually contact the interior of the syringe barrel intermittently, so long as sufficient discontinuous gaps exist to allow for sterilization of the area between the seals.

An exemplary embodiment of one syringe 40 that may be used with plunger/jacket assembly 10. Syringe 40 comprises barrel 42 having exterior surface 44 and interior surface 46. The syringe may have one or more retaining flanges 48 and a discharge aperture 50 and/or luer connection 52. In addition to or in lieu of the retaining flange(s), the syringe may have a continuous flange that encircles the syringe barrel 42.

The foregoing disclosure is illustrative of a present invention and is not to be construed as limiting thereof. Although one or more embodiments of the invention have been described, persons of ordinary skill in the art will readily appreciate that numerous modifications could be made without departing from the scope and spirit of the disclosed invention. As such, it should be understood that all such modifications are intended to be included within the scope of this invention. During the description and the drawings illustrate one or more exemplary embodiments of the present invention and are not to be construed as limiting.

What is claimed is:

1. A syringe assembly, comprising:
a barrel having a generally cylindrical main body portion having an interior surface and an exterior surface, a closed forward end having a discharge aperture, and an open rear end;
a plunger assembly located at least partially within the barrel, the plunger assembly including a plunger body and a plunger jacket at least partially covering the plunger body; wherein,
the plunger jacket comprises a conical front surface that extends radially outward at a first angle as it extends axially rearward and a cylindrical outer surface extending rearward from said conical front surface, a conical intermediate surface spaced from said conical front surface and extending radially outward at a second angle as it extends axially rearward forming a front wall of the plunger jacket therebetween, wherein said front wall has a thickness that increases as the wall extends radially outward; a cylindrical inner wall extending rearward from said intermediate surface, said cylindrical wall having a constant diameter that conforms to a corresponding surface on said plunger body, a lip extending radially inward from said cylindrical outer surface and radially inward of said cylindrical inner wall, wherein said lip forms an end of said plunger jacket; a forwardmost sealing ring protruding from a radially-outward surface in both a loaded state and an unloaded state, and at least one auxiliary sealing ring protruding from a radially-outward surface in both a loaded state and an unloaded state and spaced rearwardly of the forwardmost sealing ring, wherein said auxiliary sealing ring is spaced axially from said forwardmost sealing ring to define an annular space therebetween, and wherein said auxiliary sealing ring is located at the intersection of a line corresponding to said conical intermediate surface and an exterior of said plunger jacket, wherein said auxiliary sealing ring does not sealingly engage said wall of said cylinder in a resting state and defines a gap that allows sterilization fluid to flow in and out of said space between said sealing rings; and wherein when a force is applied to the plunger assembly to drive the plunger assembly forward; said increasingly thickening front wall is compressed by opposing forces acting thereon and creates a resulting force extending along the line of said conical intermediate surface to expand the at least one auxiliary sealing ring to form a seal between the plunger assembly and the barrel.

2. The syringe assembly of claim 1, wherein the auxiliary sealing ring contacts the interior of the syringe barrel only when the force is applied to the plunger assembly in the direction of the discharge aperture.

3. The syringe assembly of claim 2, wherein the at least one auxiliary sealing ring, in the unloaded state, includes a resting gap between the at least one auxiliary sealing ring and the interior surface of the barrel that is at least 0.001 inch.

4. The syringe assembly of claim 3, wherein the resting gap is between 0.005 inches and 0.020 inches.

5. The syringe assembly of claim 1, wherein the at least one auxiliary sealing ring at least intermittently contacts the syringe barrel at all times but forms a seal between the plunger assembly and the barrel only when the force is applied to the plunger assembly in the direction of the discharge aperture.

6. The syringe assembly of claim 1, wherein an opening angle of the front conical surface is greater than an opening angle of the intermediate conical surface.

7. The syringe assembly as defined in claim 1, wherein the front wall increasingly thickens at a uniform rate.

8. The syringe assembly as defined in claim 1, wherein the diameter of the forwardmost sealing ring in the resting state is substantially greater than the diameter of the auxiliary sealing ring in the resting state.

9. The syringe assembly as defined in claim 8, wherein the plunger jacket is constructed from an elastomeric material; and,
   wherein when force is applied to the first conical surface, the second sealing ring expands more than the first sealing ring.

* * * * *

UNITED STATES PATENT AND TRADEMARK OFFICE
CERTIFICATE OF CORRECTION

PATENT NO. : 7,955,309 B2
APPLICATION NO. : 11/279644
DATED : June 7, 2011
INVENTOR(S) : J. Michael Cude It is certified that error appears in the above-identified patent and that said Letters Patent is hereby corrected as shown below:

IN THE SPECIFICATION:

Column 3, line 5, insert --As illustrated in Figure 1, the assembly 10 generally comprises a plurality of circumferential integral sealing rings 30, 32, hereinafter referred to as "seals." Although two seals or sealing rings are illustrated, it is contemplated that any number of sealing rings may be utilized. The forwardmost seal 30 may generally contact the interior surface of the syringe barrel at all times. However, rear expandable seal 32, or auxiliary seal or sealing ring may only contact the interior surface of a syringe barrel upon the forward movement of the assembly 10 within the syringe barrel during injection of fluid. In a resting, or unloaded position, seal 32 may not contact the interior surface of a syringe barrel. As stated earlier, the advantage of such a seal 32 not contacting the syringe barrel is that this design eliminates the difficult-to-sterilize space typically between two seals. Alternatively, the auxiliary seal 32 may intermittently contact the interior surface of the barrel in the resting state, and form a seal with the barrel upon application of force $F_1$.--

Signed and Sealed this
Twenty-third Day of August, 2011

David J. Kappos
*Director of the United States Patent and Trademark Office*